United States Patent
Ashkinazi

(10) Patent No.: US 7,074,925 B1
(45) Date of Patent: Jul. 11, 2006

(54) N-SUBSTITUTED DERIVATIVES OF 5-OXYIMINOBARBITURIC ACID

(76) Inventor: Rimma Lliinichna Ashkinazi, dom 114, kv. 36, S-Peterburg, Nevsky pr (RU), 191025

( * ) Notice: Subject to any disclaimer, the term of this patent is extended or adjusted under 35 U.S.C. 154(b) by 0 days.

(21) Appl. No.: 09/701,204

(22) PCT Filed: May 26, 1998

(86) PCT No.: PCT/RU98/00160
§ 371 (c)(1),
(2), (4) Date: Jan. 12, 2001

(87) PCT Pub. No.: WO99/61427
PCT Pub. Date: Dec. 2, 1999

(51) Int. Cl.
C07D 239/52 (2006.01)
A01K 31/505 (2006.01)
A01P 31/22 (2006.01)

(52) U.S. Cl. .............. 544/299; 544/301; 544/302; 544/303; 544/304; 544/305; 514/274

(58) Field of Classification Search ............ 544/299, 544/301, 302, 303, 304, 305; 514/274
See application file for complete search history.

(56) References Cited

U.S. PATENT DOCUMENTS 5,456,904 A * 10/1995 Bush .................... 424/59

FOREIGN PATENT DOCUMENTS

WO 96 40 856 * 12/1996

* cited by examiner

*Primary Examiner*—Richard L. Raymond
*Assistant Examiner*—Venkataraman Balasubramanian
(74) *Attorney, Agent, or Firm*—I. Zborovsky

(57) ABSTRACT

N-substituted derivatives of 5-oximinobarbituric add of the general formula

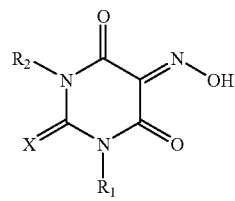

where X is sulfur; $R_1$ is selected from the group consisting of saturated or unsaturated alkyl, cycloalkyl, aryl and arylalkyl; and $R_2$ is selected from the group consisting of hydrogen, saturated or unsaturated alkyl, cycloalkyl, aryl and arylalkyl possessing a biological activity.

16 Claims, No Drawings

N-SUBSTITUTED DERIVATIVES OF 5-OXYIMINOBARBITURIC ACID

FIELD OF THE INVENTION

The present invention relates to medicine, and more specifically to pharmacology, and in particular to synthetic biologically active compounds of heterocyclic series, possessing antiviral, immune-stimulating (interferon-inducing), antichlamydial, antituberculous, antiaggregational, antiatherosclerotic, psychostimulating, psychodepressing, analgetic, hypoglycemic, antiulcerous, hepatoprotective, and antioxidant activities: derivatives of 5-oximinobarbituric acid.

Signed derivatives possess a high antiviral activity respecting to Herpes simple virus, a high activity as the interferon inductors, a high antichlamydial activity, and also antimicrobial activity respecting to mycobacteria of tuberculosis, antiaggregational, antiatherosclerotic, psychostimulating, psychodepressing, analgetic, hypoglycemic, antiulcerous, hepatoprotective, and antioxidant activities. Compounds are mainly intended for use in medicine practice to treat viral infections; the infections caused by chlamydia; the diseases followed by immune-deficiency; malignant neoplasms; tuberculosis; mycobacteriosis; myocardial infarction; diseases of liver, kidney, nervous system and others, and to use as analgetics.

Besides that, the given compounds can be used in veterinary or cosmetology for the same purposes.

TECHNICAL LEVEL

It is known that viral diseases are one of the most significant problems of modem medicine. Viral infections, for example, infections caused by viruses of the herpes group hardly respond to treatment as a rule. It is bound up with lack of efficiency of current drugs and high rate of variability of the viruses, whose mutations often lead to origin of more resistant forms [1, 2].

Viral diseases often take a course on the background of lowering activity of the immune system, and they followed by secondary infections; the same is also true for oncologic diseases. Therefore the problem of the development of effective antiviral or antitumoral drugs is closely bound up with the searching for remedies to treat the immune-deficient states of various origination. As is known, stimulators of immune system are used in treating a number of oncologic diseases.

Existing antiviral drugs may be conventionally divided into 2 groups according to types of mechanisms of their action. An action of the drugs of the first group involves suppression of virus reproduction in the organism [1]. This group includes derivatives of Adamantane (Flumadine [3]), thiosemicarbazones (Metisazone [3]); the most active are the derivatives and the analogues of the nucleosides: Acyclovir, Ganciclovir, Retrovir [1], and others. Antiviral drugs of the second group produce their effect due to the stimulation of organism's immune protection and increase of producing endogenic interferons [3] to a greater extent than due to affecting the viruses in themselves. Arbidolum [3], Neovir [4], and others belong to this type of drugs.

Despite the fact that search for antiviral and immune-stimulating remedies has been conducting intensively among the different classes of chemical compounds, the need for new drugs of such types increases, and it is bound up with insufficient efficiency of existing drugs (especially in the case of immune-deficient states) as well as advent of new forms of viruses that are resistant to the action of the known chemotherapeutic drugs. Analysis of literature demonstrates that the greatest quantity of the effective antiviral drugs was revealed among the derivatives of pyrimidine [5]. The derivatives of barbituric acid, which possess a variety of biological activities, have an significant place in the group of pyrimidine [6]. So, a number of active antiviral [7–9] and antitumoral [10, 11] agents were detected among the barbituric acids. The compounds of this class possess bacteriostatic [12, 13], anti-inflammatory [14], and immune-modulating [15] effects.

There is a reasonable group of 5-oximinobarbituric (violuric) acids among derivatives of pyrimidine. In contrast to other groups of pyrimidines and barbituric acids, violuric acid and its derivatives are investigated extremely poor in the context of biological activity. Violuric acid and some its derivations has long been known [16], however, they have been used only as analytical reagents to detect cations of some metals [17, 18]. As late as 1988 violuric acid was suggested as antidote against poisoning caused by nitrate compounds [19]. A sodium salt of 2-methylthiovioluric acid, which is another derivative of violuric acid, has been used as antiedemic agent on treating a toxic edema of lung [20]. The work [21] has shown that violuric acid is able to stabilize hemoglobin, preventing it from oxidizing to metgemoglobin in in vitro models.

Violuric acid is obtained from barbituric acid by the reaction of nitrosation [16]. The reaction is of general character; that is other N-substituted derivatives of violuric acid can be obtained the same way from the corresponding derivatives of barbituric acid. The derivatives of barbituric acid that are necessary to proceed the synthesis are obtained from the corresponding substituted carbamides. At this takes place, the method of Fisher [22] is used as a rule to obtain barbituric acids having substituent only at one nitrogen atom; that is condensation of monosubstituted carbamide with malonic ester in the presence of sodium ethylate is used. To obtain barbituric acids having two substituents at the $N^1$ and $N^3$ nitrogen atoms, condensation of the corresponded N,N'-disubstituted carbamide with malonic acid in the presence of $PCl_5$ or $POCl_3$ [23] is used. Finally, the derivatives of carbamide or thiocarbamide that are necessary to proceed the synthesis are obtained by commonly used methods described in [24].

5-oximinobarbituric (violuric) acid [16] has been taken as a prototype. The choice has been motivated by the fact that, of all known substances, violuric acid, which possesses a biological activity, is the closest by its chemical structure to the claimed substances.

OBJECTIVE OF THE INVENTION

Objective of the invention is obtaining new chemical compounds possessing antiviral activity (respecting to Herpes Simplex virus), immune-stimulating activity (at the expense of induction of producing endogenic interferons in organism), antichlamydial and antituberculous activities, and also antiaggregational, antiatherosclerotic, psychostimulative, psychodepressive, analgetic, hypoglycemic, antiulcerous, hepatoprotective, and antioxidant activities. In other words, the objective of the invention is to synthesize a biologically active substance that outperforms the prototype in its biological activity and wide range of biological action.

SUBJECT OF THE INVENTION

The proposed objective is achieved by synthesis of the group of new chemical compounds—N-substituted derivatives of 5-oximinobarbituric acid of the general formula (I)

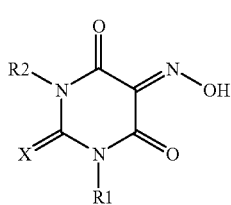

where

X is the atom of oxygen or sulfur;

R1 is taken from the group of saturated or unsaturated alkanes, cycloalkanes, arylalkanes, aromatic compounds;

R2 is the hydrogen atom or taken from the group of saturated or unsaturated alkanes, cycloalkanes, arylalkanes, aromatic compounds.

The best solution of the formulated objective by the time of the application has been applied was obtained when the following combinations:

| | |
|---|---|
| X = O, R1 = n-Bu, R2 = H (II); | X = O, R1 = t-Bu, R2 = H (III); |
| X = O, R1 = n-C$_6$H$_{13}$, R2 = H (IV); | X = O, R1 = i-C$_6$H$_{13}$, R2 = H (V); |
| X = O, R1 = n-C$_7$H$_{15}$, R2 = H (VI); | X = O, R1 = n-C$_{10}$H$_{21}$, R2 = H (VII); |
| X = O, R1 = cyclohexyl, R2 = H (VIII); | X = O, R1 = allyl, R2 = H (IX); |
| X = O, R1 = 2-(1-cyclohexenylethyl), R2 = H (X); | X = O, R1 = PhCH$_2$, R2 = H (XI); |
| X = O, R1 = p-FC$_6$H$_4$CH$_2$, R2 = H (XII); | X = 0, R1 = p-(CH$_3$O)C$_6$H$_4$CH$_2$, R2 = H (XIII); |
| X = O, R1 = PhCH$_2$CH$_2$, R2 = H (XIV); | X = O, R1 = p-FC$_6$H$_4$CH$_2$CH$_2$, R2 = H (XV); |
| X = O, R1 = Ph(CH$_3$)CH, R2 = H (XVI); | X = O, R1 = PhCH$_2$(CH$_3$)CH, R2 = H (XVII); |
| X = O, R1 = R2 = cyclohexyl (XVIII); | X = O, R1 = Ph, R2 = H (XIX); |
| X = O, R1 = o-CH$_3$C$_6$H$_4$, R2 = H(XX); | X = O, R1 = m-CH$_3$C$_6$H$_4$, R2 = H(XXI); |
| X = O, R1 = p-CH$_3$C$_6$H$_4$, R2 = H (XXII); | X = O, R1 = p-EtC$_6$H$_4$, R2 = H (XXIII); |
| X = O, R1 = 2,4,6-(CH$_3$)$_3$C$_6$H$_2$, R2 = H (XXIV); | X = O, R1 = o-FC$_6$H$_4$, R2 = H (XXV); |
| X = O, R1 = m-FC$_6$H$_4$, R2 = H (XXVI); | X = O, R1 = p-FC$_6$H$_4$, R2 = H (XXVII); |
| X = O, R1 = p-ClC$_6$H$_4$, R = H (XXVIII); | X = O, R1 = p-BrC$_6$H$_4$, R2 = H (XXIX); |
| X = O, R1 = p-(EtO)C$_6$H$_4$, R2 = H (XXX); | X = O, R1 = 2,5-(CH$_3$O)$_2$C$_6$H$_3$, R2 = H (XXXI); |
| X = O, R1 = m-(CF$_3$)C$_6$H$_4$, R2 = H (XXXII); | X = O, R1 = p-(EtOOC)C$_6$H$_4$, R2 = H (XXXIII); |
| X = O, R1 = a-naphthyl, R2 = H (XXXIV); | X = O, R1 = p-EtC$_6$H$_4$, R2 = CH$_3$ (XXXV); |
| X = S, R1 = Et, R2 = H (XXXVI); | X = S, R1 = n-C$_6$H$_{13}$, R2 = H (XXXVII); |
| X = S, R1 = cyclohexyl, R2 = H (XXXVIII); | X = S, R1 = allyl, R2 = H (XXXIX); |
| X = S, R1 = R2 = CH3 (XL); | X = S, R1 = R2 = Et (XLI); |
| X = S, R1 = o-CH$_3$C$_6$H$_4$, R2 = H (XLII); | X = S, R1 = p-CH$_3$C$_6$H$_4$, R2 = H (XLIII); |
| X = S, R1 = o-FC$_6$H$_4$, R2 = H (XLIV); | X = S, R1 = p-FC$_6$H$_4$, R2 = H (XLV); |
| X = S, R1 = p-ClC$_6$H$_4$, R2 = H (XLVI); | X = S, R1 = p-(CH$_3$O)C$_6$H$_4$, R2 = H (XLVII); |
| X = S, R1 = p-(CH$_3$O)C$_6$H$_4$, R2 = Ph (XLVIII); | X = S, R1 = R2 = o-(CH$_3$)C$_6$H$_4$ (IL); |
| X = S, R1 = R2 = p-(CH$_3$O)C$_6$H$_4$ (L). | |

The claimed compounds are new because they are not known for the applicants from available information sources.

It should be noted that use of other representatives of the groups mentioned in the formula (I) (from which the choice is done) is not of fundamental importance to solve the objective of this invention, because the fact of presence of some claimed activities is demonstrated to one or another extent by all the representatives of this group, when X, R1, R2 belong to the general formula. All the representatives of the group are also produced with the common method of synthesis. Thus, the specific structure of the R1 or R2 radicals, which influences only a quantitative level of biological activity, is not critical, but belonging these radicals to the chemical groups enumerated in the general formula (I) is of fundamental importance.

The claimed solution is not obvious. No data on antiviral, immunotropic, antichlamydial, antibacterial, antiaggregational, antiatherosclerotic, psychostimulating, psychodepressing, analgetic, hypoglycemic, antiulcerous, hepatoprotective, and antioxidant activities of 5-oximinobarbituric acid or its derivatives have not been known before. Thus, producing group of new derivatives of 5-oximinobarbituric (violuric) acid and discovery of their antiviral, immune-stimulating (interferon-inducing), antichlamydial, antituberculous, antiaggregational, antiatherosclerotic, psychostimulating, psychodepressing, analgetic, hypoglycemic, antiulcerous, hepatoprotective, and antioxidant activities do not obviously follow from modem level of technique.

DISCLOSURE OF THE INVENTION

The subject matter of the present invention is explained below by examples of synthesis of intermediate substances and a general example of synthesis of the claimed compounds, data on outputs of the intermediate and target products, data on element analysis, and results of 14 series of experiments for determination of their biological properties, where:

Examples 1 and 2 are versions of synthesizing intermediate substances (LI-IC) (versions of producing derivatives of barbituric acid that are enumerated in Tables 1 and 2). These are the examples of the first stage of synthesis of the claimed substances.

Example 3 is a version of synthesizing the claimed substances (producing target products (II-L), which are derivatives of 5-oximinobarbituric acid and that are enumerated in Table 3). This is the second stage of synthesis of the claimed substances.

Table 1. Initial substances to synthesize intermediate substances; melting points, and output of intermediate substances (LI-XCII), which are N-monosubstituted derivatives of barbituric acid.

Table 2. Initial substances to synthesize intermediate substances; melting points, and output of intermediate substances (XCIII-IC), which are N,N'-disubstituted derivatives of barbituric acid.

Table 3. Output and melting points of target products (II-L), that are N-substituted derivatives of 5-oximinobarbituric acid.

Table 4. Data on element analysis of target products (II-XXXV).

Table 5. Data on element analysis of target products (XXXVI-L).

Data of 14 series of experiments to determine biological activity of the claimed substances include the following:

Experiment 1. Determination of antimicrobial (*M. smegmatis, M. tuberculosis*) action of the claimed compounds (with Table 6).

Experiment 2. Determination of the maximal tolerant dose of the claimed compounds (with Table 7).

Experiment 3. Determination of effect of the claimed compounds on Herpes virus (with Table 8).

Experiment 4. Determination of interferon-inducing activity of the claimed compounds (with Table 9).

Experiment 5. Determination of effect of the claimed compounds on *Chlamydia trachomatis* (with Table 10).

Experiment 6. Determination of antiaggregational properties of the claimed compounds (with Table 11).

Experiment 7. Determination of antiatherosclerotic properties of the claimed compounds (with Table 12).

Experiment 8. Determination of psychostimulating activity of the claimed compounds (with Table 13).

Experiment 9. Determination of psychodepressing activity of the claimed compounds (with Table 14).

Experiment 10. Evaluation of analgetic activity of the claimed compounds (with Table 15).

Experiment 11. Evaluation of hypoglycemic activity of the claimed compounds (with Table 16).

Experiment 12. Determination of antiulcerous action of the claimed compounds (with Table 17).

Experiment 13. Determination of hepatoprotective activity of the claimed compounds (with Table 18).

Experiment 14. Determination of antioxidant action of the claimed compounds (with Table 19).

Examples of the Synthesis of the Claimed Substances

The best of the methods known to the authors consists of two stages:

1) Derivative of barbituric acid (LI-IC) is synthesized from the corresponding derivatives of carbamide (C-CXLVIII, see Tables 1 and 2) and malonic acid (CIL, CL);
2) Target substances (II-L) are produced from the intermediate substances (LI-IC) synthesized by treating them with $NaNO_2$ and acid.

The method is common to all the claimed substances.

EXAMPLE 1

Version of synthesizing intermediate substances (LI-XCII), which are N-monosubstituted derivatives of barbituric acid (version of the $1^{st}$ stage of synthesis of the claimed substances).

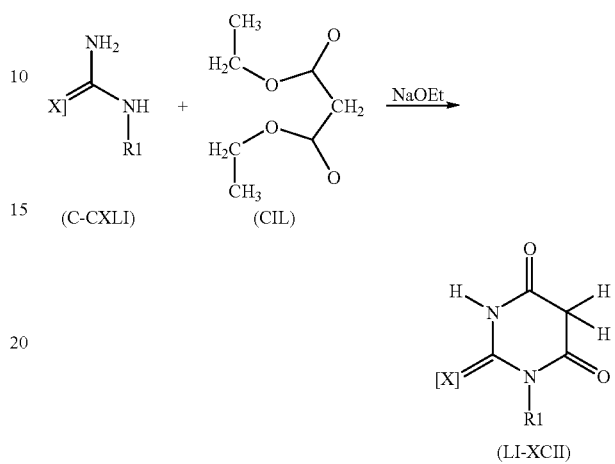

4.6 g (0.2 mol) of metallic sodium are dissolved in 100 ml of absolute ethanol. Then, 16 g (0.1 mol) of malonic ester (CIL) are added to the solution obtained, and the mixture is stirred during 5 minutes. Then 0.1 mol of carbamide derivative (C-CXLIII) is added and it is stirred during 6 hours when boiling with reverse cooler. Then the mixture is cooled to 25° C., and 30 ml of water are added. The solution is filtered to remove residue and, after that, it is acidified with HCl to pH1, cooled dawn to 5° C., and kept at this temperature for 3 hours. Precipitated residue is filtered, washed with water and dried. The product is recrystallized from alcohol. Outputs and melting points are shown in Table 1.

TABLE 1

Initial substances to synthesize intermediate substances; melting points, and output of intermediate substances (LI–XCII).

| Initial substance (derivative of carbamide) | X | R1 | Intermediate substance (derivative of barbituric acid) | Output, % | M.P., ° C. |
|---|---|---|---|---|---|
| C | O | n-Bu | LI | 35 | 104 |
| CI | O | t-Bu | LII | 9 | 146 |
| CII | O | n-$C_6H_{13}$ | LIII | 42 | 126 |
| CIII | O | i-$C_6H_{13}$ | LIV | 46 | 133 |
| CIV | O | n-$C_7H_{15}$ | LV | 49 | 141 |
| CV | O | n-$C_{10}H_{21}$ | LVI | 42 | 173 |
| CVI | O | cyclohexyl | LVII | 64 | 172 |
| CVII | O | allyl | LVIII | 62 | 146 |
| CVIII | O | 2-(1-cyclohexenylethyl) | LIX | 79 | 142 |
| CIX | O | $PhCH_2$ | LX | 72 | 146 |
| CX | O | p-$FC_6H_4CH_2$ | LXI | 73 | 149 |
| CXI | O | p-$(CH_3O)C_6H_4CH_2$ | LXII | 70 | 152 |
| CXII | O | $PhCH_2CH_2$ | LXIII | 65 | 199 |
| CXIII | O | p-$FC_6H_4CH_2CH_2$ | LXIV | 74 | 207 |
| CXIV | O | $Ph(CH_3)CH$ | LXV | 56 | 134 |
| CXV | O | $PhCH_2(CH_3)CH$ | LXVI | 44 | 128 |
| CXVI | O | Ph | LXVII | 72 | 275 |
| CXVII | O | o-$CH_3C_6H_4$ | LXVIII | 67 | 251 |
| CXVIII | O | m-$CH_3C_6H_4$ | LXIX | 55 | 115 |
| CXIX | O | p-$CH_3C_6H_4$ | LXX | 73 | 245 |

TABLE 1-continued

Initial substances to synthesize intermediate substances; melting points, and output of intermediate substances (LI–XCII).

| Initial substance (derivative of carbamide) | X | R1 | Intermediate substance (derivative of barbituric acid) | Output, % | M.P., °C |
|---|---|---|---|---|---|
| CXX | O | p-EtC$_6$H$_4$ | LXXI | 66 | 207 |
| CXXI | O | 2,4,6-(CH$_3$)$_3$C$_6$H$_2$ | LXXII | 61 | 256 |
| CXXII | O | o-FC$_6$H$_4$ | LXXIII | 69 | 193 |
| CXXIII | O | m-FC$_6$H$_4$ | LXXIV | 57 | 124 |
| CXXIV | O | p-FC$_6$H$_4$ | LXXV | 71 | 220 |
| CXXV | O | p-ClC$_6$H$_4$ | LXXVI | 72 | 235 |
| CXXVI | O | p-BrC$_6$H$_4$ | LXXVII | 70 | 224 |
| CXXVII | O | p-EtOC$_6$H$_4$ | LXXVIII | 78 | 208 |
| CXXVIII | O | 2,5-(CH$_3$O)$_2$C$_6$H$_3$ | LXXIX | 43 | 192 |
| CXXIX | O | m-(CF$_3$)C$_6$H$_4$ | LXXX | 65 | 150 |
| CXXX | O | p-(EtOOC)C$_6$H$_4$ | LXXXI | 45 | 196 |
| CXXXI | O | α-naphthyl | LXXXII | 32 | 239 |
| CXXXII | S | Et | LXXXIII | 88 | 173 |
| CXXXIII | S | n-C$_6$H$_{13}$ | LXXXIV | 84 | 197 |
| CXXXIV | S | cyclohexyl | LXXXV | 82 | 199 |
| CXXXV | S | allyl | LXXXVI | 91 | 132 |
| CXXXVI | S | o-CH$_3$C$_6$H$_4$ | LXXXVII | 68 | 202 |
| CXXXVII | S | p-CH$_3$C$_6$H$_4$ | LXXXVIII | 73 | 222 |
| CXXXVIII | S | o-FC$_6$H$_4$ | LXXXIX | 70 | 170 |
| CXXXIX | S | p-FC$_6$H$_4$ | XC | 77 | 223 |
| CXL | S | p-ClC$_6$H$_4$ | XCI | 62 | 217 |
| CXLI | S | p-(CH$_3$O)C$_6$H$_4$ | XCII | 64 | 257 |

EXAMPLE 2

Version of synthesizing intermediate substances (XCIII-IC), which are N,N'-disubstituted derivatives of barbituric acid (version of the 1$^{st}$ stage of synthesis of the claimed substances).

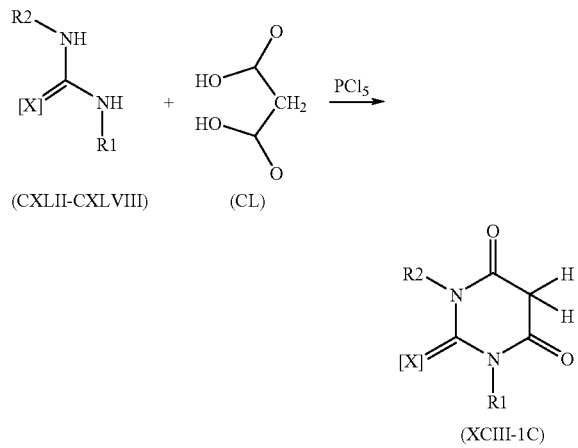

25 ml of chloroform are added to 10.4 g (0.1 mol) of malonic acid and stirred. 31.4 g (0.15 mol) of phosphorus pentachloride are added to the mixture obtained and stirred at a temperature of 40° C. to dissolve products completely. After that, 0.1 mol of carbamide derivative (CXLII-CXLVIII) is added and the mixture is stirred during 12 hours while boiling with a reverse cooler. Then the mixture is cooled to 25° C., 50 ml of water are added, stirred, and a water layer is separated. An organic layer is extracted repeatedly with 50 ml of water. Then 30 ml of 25% solution of ammonia and 50 ml of water are added to the organic layer, the mixture is thoroughly shaken and the ammonia-water layer is separated. The ammonia-water solution is held at 25° C. for 3 hours, then it is filtered to remove residue, the filtrate is acidified with HCl to pHl. Deposited precipitation is filtered, washed with water, and dried. The product is recrystallized from alcohol. Outputs and melting points are shown in Table 2.

TABLE 2

Initial substances to synthesize intermediate substances; melting points, and output of intermediate substances (XCIII–IC).

| Initial substance (derivative of carbamide) | X | R1 | R2 | Intermediate substance (derivative of barbituric acid) | Output, % | M.P., °C |
|---|---|---|---|---|---|---|
| CXLII | O | cyclohexyl | cyclohexyl | XCIII | 49 | 202 |
| CXLIII | O | p-EtC$_6$H$_4$ | CH$_3$ | XCIV | 46 | 55 |
| CXLIV | S | CH$_3$ | CH$_3$ | XCV | 58 | 188 |
| CXLV | S | Et | Et | XCVI | 59 | 97 |
| CXLVI | S | p-CH$_3$OC$_6$H$_4$ | Ph | XCVII | 74 | 129 |
| CXLVII | S | o-(CH$_3$)C$_6$H$_4$ | o-(CH$_3$)C$_6$H$_4$ | XCVIII | 71 | 137 |
| CXLVIII | S | p-(CH$_3$O)C$_6$H$_4$ | p-(CH$_3$O)C$_6$H$_4$ | IC | 70 | 227 |

EXAMPLE 3

Version of synthesizing the claimed substances (producing target products (II-L), which are derivatives of 5-oximinobarbituric acid (version of the 2$^{nd}$ stage of synthesis of the claimed substances).

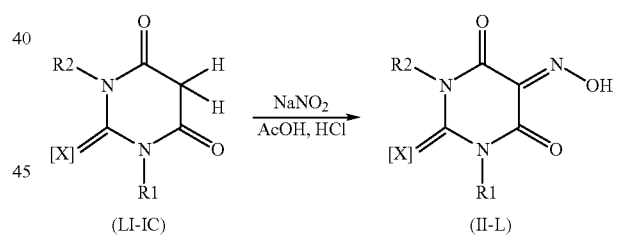

0.1 mol of derivative of barbituric acid (LI-IC) is dissolved in 60 ml of water containing 6.0 g (0.15 mol) NaOH. 10 ml of alcohol are added to the obtained transparent solution, then a solution of 7.6 g (0.11 mol) of sodium nitrite in 30 ml of water is poured in the obtained mixture, then the resulting mixture is stirred. The mixture is cooled to 10° C., then 18 g (0.3 mol) of acetic acid are added and the mixture is kept for 1 hour at 25° C. 25 ml of 30% hydrochloric acid are added to the obtained mixture and stirred during 10 minutes. Deposited precipitation is filtered, washed with 50% alcohol and, after that, with water. Product is recrystallized from aqueous alcohol and dried in vacuum in the presence of P$_2$O$_5$. Outputs and melting points are shown in Table 3, the data on element analysis are shown in Tables 4 and 5.

TABLE 3

Output and melting points of target products (II–L)

| Substance | X | R1 | R2 | Output, % | M.P., °C |
|---|---|---|---|---|---|
| II | O | n-Bu | H | 79 | 145 |
| III | O | t-Bu | H | 55 | 170 |
| IV | O | n-$C_6H_{13}$ | H | 91 | 197 |
| V | O | i-$C_6H_{13}$ | H | 91 | 202 |
| VI | O | n-$C_7H_{15}$ | H | 91 | 200 |
| VII | O | n-$C_{10}H_{21}$ | H | 92 | 194 |
| VIII | O | cyclohexyl | H | 67 | 234 |
| IX | O | allyl | H | 37 | 169 |
| X | O | 2-(1-cyclohexenylethyl) | H | 88 | 211 (p) |
| XI | O | $PhCH_2$ | H | 80 | 187 |
| XII | O | p-$FC_6H_4CH_2$ | H | 80 | 210 (p) |
| XIII | O | p-$(CH_3O)C_6H_4CH_2$ | H | 78 | 220 (p) |
| XIV | O | $PhCH_2CH_2$ | H | 92 | 195 |
| XV | O | p-$FC_6H_4CH_2CH_2$ | H | 90 | 182 |
| XVI | O | $Ph(CH_3)CH$ | H | 79 | 187 |
| XVII | O | $PhCH_2(CH_3)CH$ | H | 74 | 170 |
| XVIII | O | cyclohexyl | cyclohexyl | 79 | 225 (p) |
| XIX | O | Ph | H | 77 | 240 (p) |
| XX | O | o-$CH_3C_6H_4$ | H | 78 | 211 |
| XXI | O | m-$CH_3C_6H_4$ | H | 72 | 203 |
| XXII | O | p-$CH_3C_6H_4$ | H | 82 | 235 (p) |
| XXIII | O | p-$EtC_6H_4$ | H | 84 | 235 (p) |
| XXIV | O | 2,4,6-$(CH_3)_3C_6H_2$ | H | 93 | 155 |
| XXV | O | o-$FC_6H_4$ | H | 75 | 230 (p) |
| XXVI | O | m-$FC_6H_4$ | H | 77 | 193 |
| XXVII | O | p-$FC_6H_4$ | H | 78 | 240 (p) |
| XXVIII | O | p-$ClC_6H_4$ | H | 91 | 240 (p) |
| XXIX | O | p-$BrC_6H_4$ | H | 94 | 248 (p) |
| XXX | O | p-$(EtO)C_6H_4$ | H | 90 | 198 |
| XXXI | O | 2,5-$(CH_3O)_2C_6H_3$ | H | 81 | 174 |
| XXXII | O | m-$(CF_3)C_6H_4$ | H | 83 | 260 (p) |
| XXXIII | O | p-$(EtOOC)C_6H_4$ | H | 66 | 215 (p) |
| XXXIV | O | α-naphtyl | H | 90 | 198 |
| XXXV | O | p-$EtC_6H_4$ | $CH_3$ | 91 | 120 |
| XXXVI | S | Et | H | 90 | 190 (p) |
| XXXVII | S | n-$C_6H_{13}$ | H | 91 | 190 (p) |
| XXXVIII | S | cyclohexyl | H | 90 | 196 (p) |
| XXXIX | S | allyl | H | 78 | 179 (p) |
| XL | S | $CH_3$ | $CH_3$ | 74 | 115 |
| XLI | S | Et | Et | 79 | 110 |
| XLII | S | o-$CH_3C_6H_4$ | H | 89 | 170 (p) |
| XLIII | S | p-$CH_3C_6H_4$ | H | 89 | 190 (p) |
| XVIV | S | o-$FC_6H_4$ | H | 86 | 156 (p) |
| XVV | S | p-$FC_6H_4$ | H | 88 | 198 (p) |
| XLVI | S | p-$ClC_6H_4$ | H | 87 | 216 (p) |
| XLVII | S | p-$(CH_3O)C_6H_4$ | H | 90 | 145 (p) |
| XLVIII | S | p-$(CH_3O)C_6H_4$ | Ph | 91 | 184 |
| IL | S | o-$(CH_3)C_6H_4$ | o-$(CH_3O)C_6H_4$ | 76 | 188 |
| L | S | p-$(CH_3O)C_6H_4$ | p-$(CH_3O)C_6H_4$ | 74 | 212 (p) |

TABLE 4

Data on element analysis of target products (II–XXXV) that are derivatives of 5-oximinobarbituric acid

| Substance | Has been found, % | | | | Empirical formula | Has been calculated, % | | | |
|---|---|---|---|---|---|---|---|---|---|
| | C | H | Hal | N | | C | H | Hal | N |
| II | 45.01 | 5.24 | — | 19.67 | $C_8H_{11}N_3O_4$ | 45.07 | 5.20 | — | 19.71 |
| III | 45.00 | 5.25 | — | 19.66 | $C_8H_{11}N_3O_4$ | 45.07 | 5.20 | — | 19.71 |
| IV | 49.80 | 6.24 | — | 17.41 | $C_{10}H_{15}N_3O_4$ | 49.79 | 6.27 | — | 17.42 |
| V | 49.80 | 6.29 | — | 17.40 | $C_{10}H_{15}N_3O_4$ | 49.79 | 6.27 | — | 17.42 |
| VI | 51.79 | 6.70 | — | 16.44 | $C_{11}H_{17}N_3O_4$ | 51.76 | 6.71 | — | 16.46 |
| VII | 56.61 | 7.83 | — | 14.10 | $C_{14}H_{23}N_3O_4$ | 56.55 | 7.80 | — | 14.13 |
| VIII | 50.25 | 5.44 | — | 17.52 | $C_{10}H_{13}N_3O_4$ | 50.21 | 5.48 | — | 17.56 |
| IX | 38.61 | 4.14 | — | 19.33 | $C_7H_7N_3O_4 \cdot H_2O$ | 38.71 | 4.18 | — | 19.35 |
| X | 54.31 | 5.72 | — | 15.79 | $C_{12}H_{15}N_3O_4$ | 54.33 | 5.70 | — | 15.84 |
| XI | 53.41 | 3.65 | — | 16.99 | $C_{11}H_9N_3O_4$ | 53.44 | 3.67 | — | 17.00 |
| XII | 49.81 | 3.04 | 7.15 | 15.81 | $C_{11}H_8FN_3O_4$ | 49.82 | 3.04 | 7.16 | 15.85 |
| XIII | 52.00 | 4.01 | — | 15.13 | $C_{12}H_{11}N_3O_5$ | 51.99 | 4.00 | — | 15.16 |
| XIV | 55.19 | 4.22 | — | 16.06 | $C_{12}H_{11}N_3O_4$ | 55.17 | 4.24 | — | 16.09 |
| XV | 51.60 | 3.60 | 6.78 | 15.04 | $C_{12}H_{10}FN_3O_4$ | 51.62 | 3.61 | 6.80 | 15.05 |
| XVI | 55.14 | 4.25 | — | 16.05 | $C_{12}H_{11}N_3O_4$ | 55.17 | 4.24 | — | 16.09 |
| XVII | 56.69 | 4.79 | — | 15.25 | $C_{13}H_{13}N_3O_4$ | 56.72 | 4.76 | — | 15.27 |
| XVIII | 59.77 | 7.22 | — | 13.04 | $C_{16}H_{23}N_3O_4$ | 59.80 | 7.21 | — | 13.08 |
| XIX | 51.53 | 3.05 | — | 18.01 | $C_{10}H_7N_3O_4$ | 51.51 | 3.03 | — | 18.02 |
| XX | 53.41 | 3.68 | — | 16.98 | $C_{11}H_9N_3O_4$ | 53.44 | 3.67 | — | 17.00 |
| XXI | 53.40 | 3.69 | — | 16.99 | $C_{11}H_9N_3O_4$ | 53.44 | 3.67 | — | 17.00 |
| XXII | 53.42 | 3.67 | — | 17.99 | $C_{11}H_9N_3O_4$ | 53.44 | 3.67 | — | 17.00 |
| XXIII | 55.16 | 4.24 | — | 16.08 | $C_{12}H_{11}N_3O_4$ | 55.17 | 4.24 | — | 16.09 |
| XXIV | 56.70 | 4.79 | — | 15.24 | $C_{13}H_{13}N_3O_4$ | 56.72 | 4.76 | — | 15.27 |
| XXV | 49.76 | 2.53 | 7.87 | 17.40 | $C_{10}H_6FN_3O_4$ | 49.80 | 2.51 | 7.88 | 17.42 |
| XXVI | 49.82 | 2.52 | 7.86 | 17.40 | $C_{10}H_6FN_3O_4$ | 49.80 | 2.51 | 7.88 | 17.42 |
| XXVII | 49.81 | 2.53 | 7.86 | 17.40 | $C_{10}H_6FN_3O_4$ | 49.80 | 2.51 | 7.88 | 17.42 |
| XXVIII | 44.84 | 2.28 | 13.21 | 15.66 | $C_{10}H_6ClN_3O_4$ | 44.88 | 2.26 | 13.25 | 15.70 |
| XXIX | 38.47 | 1.96 | 25.59 | 13.43 | $C_{10}H_6BrN_3O_4$ | 38.49 | 1.94 | 25.60 | 13.46 |
| XXX | 51.95 | 4.02 | — | 15.14 | $C_{12}H_{11}N_3O_5$ | 51.99 | 4.00 | — | 15.16 |
| XXXI | 49.12 | 3.81 | — | 14.30 | $C_{12}H_{11}N_3O_6$ | 49.15 | 3.78 | — | 14.33 |
| XXXII | 43.82 | 2.03 | 18.90 | 13.93 | $C_{11}H_6F_3N_3O_4$ | 43.87 | 2.01 | 18.93 | 13.95 |
| XXXIII | 51.01 | 3.72 | — | 13.72 | $C_{13}H_{11}N_3O_6$ | 51.15 | 3.63 | — | 13.77 |
| XXXIV | 59.32 | 3.24 | — | 14.81 | $C_{14}H_9N_3O_4$ | 59.36 | 3.20 | — | 14.84 |
| XXXV | 56.70 | 4.79 | — | 15.24 | $C_{13}H_{13}N_3O_4$ | 56.72 | 4.76 | — | 15.27 |

TABLE 5

Data on element analysis of target products (XXXVI–L), that are derivatives of 2-thio-5-oximinobarbituric acid

| Product | Has been found, % | | | | | Empiric formula | Has been calculated, % | | | | |
|---|---|---|---|---|---|---|---|---|---|---|---|
| | C | H | Hal | N | S | | C | H | Hal | N | S |
| XXXVI | 35.77 | 3.56 | — | 20.80 | 15.91 | $C_6H_7N_3O_3S$ | 35.82 | 3.51 | — | 20.89 | 15.94 |
| XXXVII | 46.39 | 5.94 | — | 16.31 | 12.44 | $C_{10}H_{15}N_3O_3S$ | 46.48 | 5.88 | — | 16.33 | 12.46 |
| XXXVIII | 46.99 | 5.23 | — | 16.33 | 12.46 | $C_{10}H_{13}N_3O_3S$ | 47.05 | 5.13 | — | 16.45 | 12.56 |
| XXXIX | 39.41 | 3.33 | — | 19.70 | 15.02 | $C_7H_7N_3O_3S$ | 39.44 | 3.31 | — | 19.71 | 15.04 |
| XL | 35.80 | 3.54 | — | 20.82 | 15.88 | $C_6H_7N_3O_3S$ | 35.82 | 3.51 | — | 20.89 | 15.94 |
| XLI | 42.21 | 4.92 | — | 18.42 | 14.06 | $C_8H_{11}N_3O_3S$ | 42.29 | 4.88 | — | 18.49 | 14.11 |
| XLII | 50.07 | 3.49 | — | 15.90 | 12.11 | $C_{11}H_9N_3O_3S$ | 50.18 | 3.45 | — | 15.96 | 12.18 |
| XLIII | 50.09 | 3.48 | — | 15.91 | 12.12 | $C_{11}H_9N_3O_3S$ | 50.18 | 3.45 | — | 15.96 | 12.18 |
| XLIV | 46.64 | 2.38 | 7.36 | 16.32 | 12.43 | $C_{10}H_6FN_3O_3S$ | 46.69 | 2.35 | 7.3 | 16.34 | 12.46 |
| XLV | 46.67 | 2.36 | 7.39 | 16.34 | 12.44 | $C_{10}H_6FN_3O_3S$ | 46.69 | 2.36 | 7.3 | 16.34 | 12.46 |
| XLVI | 42.31 | 2.17 | 2.49 | 14.78 | 11.27 | $C_{10}H_6ClN_3O_3S$ | 42.34 | 2.13 | 12. | 14.81 | 11.30 |
| XLVII | 47.30 | 3.25 | — | 15.04 | 11.47 | $C_{11}H_9N_3O_4S$ | 47.31 | 3.25 | — | 15.05 | 11.48 |
| XLVIII | 57.41 | 3.73 | — | 11.78 | 9.00 | $C_{17}H_{13}N_3O_4S$ | 57.46 | 3.69 | — | 11.82 | 9.02 |
| IL | 61.11 | 4.33 | — | 11.80 | 9.01 | $C_{18}H_{15}N_3O_3S$ | 61.18 | 4.28 | — | 11.89 | 9.07 |
| L | 56.06 | 3.94 | — | 10.85 | 8.28 | $C_{18}H_{15}N_3O_5S$ | 56.10 | 3.92 | — | 10.90 | 8.32 |

Experimental Testing Biological Activity of the Claimed Compounds

Experiment 1. Determination of Antimicrobial (*M. smegmatis, M. tuberculosis*) Action of the Claimed Compounds To determine an antimicrobial activity a standard strains *Mycobacterium smegmatis* ATCC607 and *Mycobacterium tuberculosis* H37RV sensitive to all the antimicrobial agents were used. Antimycobacterial action was estimated by the serial dilution method [1]. For seeding, *M. smegmatis* ATCC607 were grown in a synthetic liquid medium N-1. Substances were dissolved in dimethyl-sulfoxide (DMSO) and diluted in the medium N-1, so that the preparation was contained in separate test tubes with the medium in concentrations from 200 to 0.025 mg/l. The concentrations of the substance in the medium in adjacent test tubes differed by the factor of two. DMSO diluted in the same way as the substance was utilized for the control. The test strain of bacteria was added in amounts of $1-2 \times 10^6$ ml. The result was considered after a 72-hour cultivation of the test tubes at 37° C.

For *M. tuberculosis* H37Rv conditions for the experiment were identical, with the exception of the fact that bacteria were grown on the Soton medium which contains 10% of horse serum, and the density of microbial suspension when seeding was $50 \times 10^6$ cell/ml.

In both cases known tuberculostatic compounds were utilized as the control. The results obtained for the used strains are summarized in the Table 6.

TABLE 6

Minimal ingibitory concentrations (MIC) relative to M. tuberculosis H37R and M. smegmatis ATCC 607 (mg/l)

| NN | Composition | MIC | |
|---|---|---|---|
| | | M. tuberculosis | M. smegmatis |
| 1. | XL | 12.5 | 3.1 |
| Controls | | | |
| 1. | Streptomycin | 0.2 | 0.15 |
| 2. | Isoniazid | 0.1 | 1.5 |
| 3. | Rifamycin | 0.05 | 0.25 |
| 4. | Ethambutol | 5.0 | 5.0 |
| 5. | Ofloxacin | 0.5 | 0.5 |

The data shown in Table 6 indicate that the substance XL possesses antibacterial activity relative to the used strains of mycobacteria in concentrations from 3.0 to 12.5 mg/l.

Other claimed substances possess less antimicrobial activity.

Experiment 2. Determination of Maximal Tolerable Dose

Tested substance was introduced perorally (in dose of 300 mg/kg) through a gastric tube or intraperitoneally (in dose of 100 mg/kg) to no-breed white mice with mass 18–20 g (each tested group consisted of 3 males and 3 females). Then the mouse state was observed during 72 hours. Absence of symptoms characteristic of toxic effects, or absence of animal death during the given time allows to make a conclusion that the toxicity of the test substance is low. If acute toxicity effects are observed, the dose is reduced to find maximal tolerable dose [25].

TABLE 7

Maximal tolerable dose in the case of oral administration

| NN | Substance | Concentration of test substances (mg/l) |
|---|---|---|
| 1 | Tween 80 | 300* |
| 2 | XXVI | 300 |
| 3 | XXIX | 300 |
| 4 | XXXII | 300 |
| 5 | XLII | 300 |

*In all the cases including the control the concentration of 300 mg/l was the maximally utilized one.

The obtained results show that the claimed substances given in the dose of 300 mg/l by oral administration do not possess an acute toxicity on mice.

Experiment 3. Determination of Effect of the Claimed Compounds on Herpes Virus

An antiviral activity was determined with respect to Herpes virus of the type I (HSV-I/Leningrad/248/88) by means of commonly accepted method [26]. Viruses were grown on a continuous culture of Vero cells that have been received from the Bank of Cell Cultures of the Institute of Cytology of the Russian Academy of Science.

Scheme of an Experiment

A virus in a final concentration of 10 particle/ml and the claimed compounds dissolved in DMSO in final concentrations of 100, 10 and 1 mg/l were added to cells that were grown on the RPMI-1640 medium with 10% fetal calf serum and placed into wells of the 96-well plate. 5 separate wells were used for each of tested concentrations of an agent. The plate was incubated during 60 minutes at 38° C. in a $CO_2$-incubator. After the incubation, the virus was removed and then a fresh medium containing claimed compounds in used concentrations was again introduced.

Results were evaluated basing on presence of cytopathogenic action on the cells after 36 hours of incubation at 38° C. in the $CO_2$-incubator.

The next controls were used in the experiment:
1. Control of cell culture (capability to grow properly)
2. Control of the virus (evaluation of capability for reproduction)
3. Control of an antiviral activity of an antiviral drug Acyclovir
4. Control of compounds (toxicity of compounds)
5. Control of a solvent (DMSO) for toxicity.

To estimate a cytopathic action of the virus, a quantity of the unchanged cells was calculated in 100 visual fields formed by a special net of an eyepiece of the inverted microscope. The data obtained are shown in Table 8.

TABLE 8

Effect of the claimed compounds (100 µg/ml) on the Herpes Simplex virus.

| NN | Substance | Quantity of the Unchanged cells (percentage of protection) |
|---|---|---|
| 1. | Acyclovir | 8000* (10 mg/mL) (80%)** |
| 2. | DMSO | 10000 |
| 3. | III | 5000 (50%) |
| 4. | XI | 3500 (35%) |
| 5. | XII | 4000 (40%) |
| 6. | XIII | 4500 (45%) |
| 7. | XV | 4000 (40%) |
| 8. | XX | 3500 (35%) |
| 9. | XXVII | 6500 (65%) |
| 10. | XXIX | 3000 (30%) |
| 11. | XXX | 3000 (30%) |
| 12. | XXXII | 5000 (50%) |
| 13. | XLII | 5000 (50%) |
| 14. | Cell control | 10000 |

\* - number of cells in 100 visual fields under consideration
\*\* - the percentage of protection of cells from virus as compared to the control of cell culture is shown in brackets.

The obtained results show that the claimed compounds presented in Table 8 possess antiherpetic activity which is comparable with that of a standard drug Acyclovir. The remainder of the claimed compounds have demonstrated the less marked activity in the process of suppressing reproduction of Herpes virus in the adopted experimental conditions.

Experiment 4. Determination of Interferon-inducine Activity of the Claimed Compounds Interferon synthesis induction caused by the claimed compounds was conducted on a primary culture of human lymphocytes (it is these cells in a human organism that are the main producers of interferons). To obtain lymphocyte culture, fresh blood (within 12 hours after sampling) from healthy donors (not of group II) was used. To separate lymphocytes, heparinized blood obtained from healthy donor was centrifuged in a density gradient of ficoll-verografin of 1.71 $g/cm^3$ in order to extract a fraction of immunocompetent cells. This fraction was selected and diluted with the nutrient medium RPMI-1640, containing 5% of fetal calf serum, 0.3 mg/ml of L-glutamin, 100 un/ml of penicillin, and 50 mg/ml of streptomycin. The concentration of lymphocytes was considered after dying them with methylene blue and calculation of cell number in Goryaev chamber. Initial solutions of the claimed compounds were diluted with the nutrient medium RPMI-1640 so that the final concentrations of the compounds, which were obtained after introduction of lymphocyte suspension, constituted the raw: 100 µg/ml, 10 µg/ml, 1 µg/ml. The final concentration of lymphocytes in the induction mixture was $3 \times 10^6$ cell/ml.

In parallels to the test samples the following controls were done:
1). Control of spontaneous production of interferons (IFN) by lymphocytes.
2). Control of the process course under the action of the standardized IFN inducer N-methyl-N-(α-D-glucopyranosil)ammonium-10-methylenecarboxylate acridone (Cyclopherone).
3). Control of the process course under the action of the standardized IFN inducer Neovir (sodium 10-methylenecarboxylate-9-acridone) with corresponding content of DMSO in experimental samples.
4). Control of spontaneous production of interferons in presence of DMSO taken in an amount corresponding to the test samples.

Control and test samples were incubated for 24 hours at the temperature of 37° C. After incubation, the samples were centrifuged at 2,000 G to deposit cell elements, and IFN-containing supernatant was separate out of samples; then the supernatant was analyzed for the quantitative content of IFN. Cell deposition was resuspended in the previous volume of nutrient medium, coloured with vital dye trypan blue, and cell number was counted in the Goryaev chamber (as described above) to determine cytotoxic action of the compounds. The quantitative determination of content of IFN in control and test samples was conducted using the immunoenzyme test system Pro Con IF2 Plus, that is intended for determination of IFN-α, which is produced by TOO "Protein contour". The solid-phase immunoenzyme method, utilizing horse radish peroxidase as an indicator enzyme, was used to determine the quantity of interferon in the samples. Activity of the bonded peroxidase was measured using an automatic photometer for microplates with a microprocessor at the wavelength of 450 nm.

To calculate the results, the activity of IFN in standard IFN solutions containing known quantities of preparation was determined in parallel. Based on the obtained results, a calibrating curve was formed, which allows to obtain data expressed in international units (IU) of activity, using the microprocessor of the automatic photometer. The results of the analysis are expressed in IU of activity of IFN per ml in the given induction system, which contains $3 \times 10^4$ lymphocyte/ml. Each test and control point was investigated in four parallels.

Controls of immunoenzyme reaction:
1. Control of DMSO with a nutrient medium.
2. Control of system components (according to an instruction). All results were considered only if controls complied with passport data of the system.

The obtained data were undergone a statistical analysis using t-criterion, and calculation of the confident interval of probability at p=0.05 was carried out. Coincidence of results in the parallel tests was analyzed.

As a result of the performed investigations, it was determined that, among the claimed substances, there are samples possessing capability to induce synthesis of IFN (Table 9).

TABLE 9

Quantitative evaluation of IFN-inducing activity of the claimed compounds

| | | Content of IFN in induction mixture after 24-hour incubation at various concentrations (µg/ml) of substances, IU/3 × $10^4$ lymph./ml | | |
|---|---|---|---|---|
| N | Substance | 100 mg/l | 10 mg/l | 1 mg/l |
| 1. | Control of lymphocytes | 0 | 0 | 0 |
| 2. | Cycloferon | 58 ± 1.4 | 22.0 ± 2.5 | 3.8 ± 0.8 |
| 3. | Neovir | 66 ± 1.4 | 24.5 ± 1.2 | 4.1 ± 0.5 |
| 4. | Poly I/poly C | —* | 43.6 ± 2.0 | 10.5 ± 0.8 |
| 5. | DMSO | 0 | 0 | 0 |
| 6. | III | 65 ± 1.2 | 23.5 ± 1.2 | 4.2 ± 0.8 |
| 7. | X | 30 ± 1.8 | 11.0 ± 1.2 | 8.6 ± 1.0 |
| 8. | XI | 60 ± 1.8 | 53.5 ± 1.2 | 32.8 ± 1.0 |
| 9. | XVII | 19.2 ± 1.2 | 13.0 ± 2.5 | 6.2 ± 0.5 |
| 10. | XXXII | 126.5 ± 1.6 | 77.5 ± 1.5 | 12.5 ± 1.0 |
| 11. | XXXVI | 26.0 ± 1.4 | 6.8 ± 1.5 | 5.2 ± 1.0 |
| 12. | XL | 22.8 ± 1.0 | 11.3 ± 1.5 | 5.1 ± 1.0 |
| 13. | XLII | 97.5 ± 1.8 | 45 ± 1.2 | 28.0 ± 1.5 |
| 14. | XLVI | 52.1 ± 1.8 | 24.4 ± 1.4 | 6.6 ± 0.8 |

* - Compound of given concentration was not tested

Stimulators of the immune system are used during treating of a number of oncological diseases.

Experiment 5. Determination of Action of the Claimed Compounds on *Chlamydia trachomatis*

The antimicrobial activity of the claimed compounds was studied relative to *C.trachomatis* D323, which is a standard strain from the collection of the chair of microbiology of St. Petersburg State Pavlov Medical University. This strain was derived from a patient with chlamydial urethritis, and it has a morphology and physiological activity that are characteristic for representatives of this type; it is sensitive to action of compounds used for treatment of chlamydial infection. Cell cultures McCoy and L929 obtained from the Institute of Cytology of RAS were used in this work.

Scheme of an Experiment

Cells were grown in flasks made of neutral glass in the medium RPMI-1640 with the addition of 10% of fetal calf serum. The test was performed in glass (non-toxic) flat-bottom flasks with cover glasses. The cells were introduced into the medium in the final concentration of 1×10 cell/ml. After a monolayer had been obtained. standard infectious dosages of chlamydia, which had been stored in a frozen state at the temperature of −70° C., were introduced into test tubes. Simultaneously, tested compounds in a final concentration of 100 mg/l were added to the cells. The sample was centrifuged at 2400 G during 60 minutes at room temperature and incubated at 37° C. for 2 hours. After this, the nutrient medium was replaced with a new medium, containing 5% of fetal calf serum and cycloheximide (2 µg/ml), with repeated introduction of the claimed compounds in the same concentration. The samples were doubled using the medium without cycloheximide so as to exclude its effect on the investigated compounds. The samples were incubated in a $CO_2$-incubator for 48 hours.

The controls included: control of cell cultures, control of action of solvents, control of action of chlamydia in absence of any compounds, control of sensitivity of chlamydia to standard antimicrobial compound Ciprofloxacin [15], control of the tested compounds for toxicity relative to the cell cultures.

The evaluation of the results was carried out by the way of determination of chlamydial cytoplasmatic inclusions (CPI) that was conducted by the method of immunofluorescence (MicroTrack *Chlamydia trachomatis* Direct Specimen Test), and by the way of determination of chlamydia antigens that was conducted by means of CylaMonoScreen (Russian-British Joint Venture 66 Regent's Pare Road London NW1 7SX) [27, 28]. The effect of the action of substance was determined by analysis of the monolayer state and number of cells with CPI when compared with the control (cell culture infected with *C.trachomatis* D323); in doing so, the number of unchanged cells, that were counted in 100 visual fields obtained using the special net of the microscope eyepiece, was taken into consideration.

Results of the control samples satisfying to the requirements of the experiment, are the following. Control of cell culture: morphology of cells and state of monolayer correspond to the given type of the cells; control of chlamydia growth in the cell culture: presence of CPI in the monolayer; control of action of standard antimicrobial agent: reduction of number of CPI in the monolayer as compared to the previous control; control of toxicity of the claimed compounds: toxicity is absent; control of action of solvents: toxic action on cells is absent. The results of performed tests are presented in Table 10.

TABLE 10

Effect of claimed substances on C. trachomatis

| NN | Substance | Number of unchanged cells |
|---|---|---|
| 1. | Cell control | 8.000 |
| 2. | DMSO | 8.000 |
| 3. | Control of infected cells | 6.000 |
| 4. | Ciprofloxacin (100)* | 7.000 (50%)** |
| 5. | III | 7.000 (50%) |
| 6. | XII | 6.600 (30%) |
| 7. | XIII | 7.000 (50%) |
| 8. | XVII | 6.700 (35%) |
| 9. | XXVII | 7.300 (65%) |
| 10. | XXX | 6.700 (35%) |
| 11. | XXXIV | 6.700 (35%) |
| 12. | XXXIX | 7.300 (65%) |
| 13. | XLII | 7.200 (60%) |

* - concentration of the preparation, mg/l
** - percentage of cell protection from infection is given in brackets, The data obtained give an evidence of the fact that the claimed compounds shown in Table 10 are of marked biological activity against chlamydia, and this activity is superior to the activity of the standard agent Ciprofloxacin.

The remaining claimed compounds possess less marked activity as to protection of cells from chlamydia in the adopted conditions of experiment.

Besides the above-stated activities, other kinds of bioactivity of the claimed substances were discovered, particularly they are antiaggregational, antiatherosclerotic, phsycostimulative, psychodepressing, anticonvulsive, analgetic, hypoglycemic, antiulcerous, hepatoprotective, and antioxidant activities. The experimental data given below prove this assertion.

Experiment 6. Determination of Antiaggregational Properties of the Claimed Compounds Human's platelet aggregation was investigated in plasma of healthy 50±3 years donors that was enriched by thrombocytes, by means of aggregometer FRM-1. The substance under investigation was added to blood plasma samples (100 μg/ml) before inducing aggregation by means of adenosine diphosphate (2.5 μmol/l). Magnitude of a maximum non-reversible platelet aggregation in the control samples (solvent) was adopted as 100%, and that in tested samples was counted as the percentage compared to the control. Inhibition of the aggregation by more than 50% at the given concentration was evaluated as meaningful inhibition. Adenosine (5 μg/ml) and aspirin (9 μg/ml), that inhibit aggregation at these concentrations by 100%, were utilized as reference agents.

TABLE 11

Antiaggregational action of the claimed substances.

| Substance | Concentration, μg/ml | % of inhibition |
|---|---|---|
| VIII | 100 | 68.9 ± 5.3 |
| XXVII | 100 | 24.3 ± 4.8 |
| XXIX | 100 | 16.4 ± 3.1 |
| XXXII | 100 | 64.3 ± 6.2 |
| XLII | 100 | 35.8 ± 3.2 |
| Adenosine | 5 | 100 |
| Aspirin | 9 | 100 |

Experiment 7. Determination of Antiatherosclerotic Properties of the Claimed Compounds Influence of the substance (400 ng/ml) on cholesterol synthesis by human's fibroblasts was investigated. The tested substance was added to the fibroblast culture, then, after an hour of incubation, [2-$^{14}$C] acetate was introduced into the medium, and it was incubated for 4 hours. After washing a monolayer, lipids were extracted from cells by means of hexane-isopropanol (3:2) mixture. Extractions were dried in the nitrogen flow and then separated by thin-layer chromatography on silica gel in system of petroleum ether—diethyl ether—ice acetic acid (90:10:1). The spots corresponding to cholesterol were removed from a plate to a vial and then were coated with scintillation liquid; after that radioactivity was measured expressed as pulse/min/mg of cell protein. Lovastatin taken in the same concentration as the tested substance was utilized as a reference agent.

TABLE 12

Inhibition of cholesterol synthesis in human's fibroblasts.

| Substance | % of inhibition |
|---|---|
| XXXII | 23.5 |
| Lovastatin | 76.4 |

Experiment 8. Determination of Psychostimulating Activity of the Claimed Compounds 10 symptoms that can demonstrate the possibility of psychostimulation were estimated in experiments on mice. The absence of a symptom was signed as "0". A maximum effect was marked as 30 points (1×10×3 mice). Results more than 12 points were considered as significant. The tested substances were administered perorally in dose of 300 mg/kg. An animal's activity was estimated before and one hour after introduction of the substance. Apomorphine was utilized as a reference agent.

TABLE 13

Psychostimulative action of the claimed substances.

| Substance | Number of points |
|---|---|
| XLII | 15 |
| Apomorphine | 19 |

Experiment 9. Determination of Psychodepressive Activity of the Claimed Compounds 10 parameters that can demonstrate possible development of behavioral depression were estimated in experiments on mice. Each parameter scores 2 points for an each mouse that had unchanged behavior. The total point sum was 60 (2×10×3 mice). Reducing score to less than 40 one hour after dosing with a substance per oral (300 mg/kg) denoted significant behavioral depression. Haloperidol was utilized as a reference agent.

TABLE 14

Psychodepressive action of the claimed substances.

| Substance | Point number |
|---|---|
| XXVII | 31 |
| XXIX | 32 |
| Haloperidol | 27 |

Experiment 10. Evaluation of Analgesic Activity of the Claimed Compounds

The time needed to draw back a tail placed under a directed source of radiant heat was estimated in a group of 3 mice. Prolongation of the response time by more than 50% after intraperitoneal dosing a substance (30 mg/kg) indicated analgesic activity. Morphine sulfate (2 mg/kg) was utilized as a reference agent.

TABLE 15

Evaluation of analgesic action of the claimed compounds.

| | Latent period of response | |
|---|---|---|
| Substance | Before dosing | 30 minutes after dosing |
| Tween-80 | 7.0 | 6.4 |
| XLII | 7.8 | 11.3 |
| Morphine | 8.3 | 14.6 |

Experiment 11. Evaluation of Hypoglycemic Activity of the Claimed Compounds

Test substance (100 mg/kg) was perorally administered to fasted mice, and, immediately after that, solution of glucose (1000 mg/kg) was administered subcutaneously. Glucose content in blood was determined in a hour by the orthotoluidine method. Reducing of glucose level by more than 20% relative to control animals indicated hypoglycemic properties. Glibenclamide (1 mg/kg) was utilized as a reference agent. Experimental results are shown in Table 16.

TABLE 16

Evaluation of hypoglycemic action of the claimed compounds.

| Substance | Glucose, mmol/l | % |
|---|---|---|
| Tween-80 | 5.81 ± 0.28 | |
| Glucose, 1000 mg/kg | 8.26 ± 0.50 | 100 |

TABLE 16-continued

Evaluation of hypoglycemic action of the claimed compounds.

| Substance | Glucose, mmol/l | % |
|---|---|---|
| Glibenclamide | 4.95 ± 0.31 | −40 |
| VIII | 6.77 ± 0.61 | −18 |
| XXVII | 7.26 ± 0.41 | −12 |
| XXXII | 7.10 ± 0.28 | −14 |

Experiment 12. Determination of Antiulcerous Action of the Claimed Compounds

Antiulcerous activity of substances was tested on a model of experimental water immersion stress with immobilization. The tested substances were administrated perorally to 3 fasted rats in a dose of 20 mg/kg 30 minutes before immobilizasion and immersion them in a wire mesh with water at 24° C. to the level of *Hiphoideus processus* for four hours. After that, gastric mucous membrane was investigated, number and sizes of ulcers were counted, ulceration index was determined (an average sum of ulcer lengths per one animal in a group). Chlorpromazine in a dose of 20 mg/kg was utilized as a reference agent. Inhibition of the ulceration index by more than 50% in the absence of hyperemia denoted as significant result. Experimental results are shown in Table 17.

TABLE 17

Estimation of antiulcerous action of the claimed compounds

| Substance | % of animals with ulcers | Number of lesions | ulceration index | % of reducing number of ulcers | % of reducing ulceration index | hyperemia |
|---|---|---|---|---|---|---|
| Control | 100 | 8.3 ± 2.5 | 10.5 ± 5.7 | | | ++ |
| VIII | 100 | 3.0 ± 1.3 | 6.8 ± 4.4 | −64 | −35 | − |
| XXVII | 67 | 1.7 ± 1.3 | 1.3 ± 1.0 | −79 | −88 | − |
| XXXII | 100 | 4.0 ± 1.3 | 3.8 ± 1.5 | −52 | −64 | +++ |
| Chlorpromazine | 33 | 0.3 ± 0.3 | 0.3 ± 0.3 | −96 | −97 | − |

Experiment 13. Determination of Hepatoprotective Activity of the Claimed Compounds $CCl_4$ dissolved in 50% olive oil (1 ml/kg) was subcutaneously administrated to rats. Test substances were administrated perorally in a dose of 20 mg/kg 30 minutes before and 7 hours after the $CCL_4$ administration. The activity of alanine-aminotranspherase (AlAT), which is a marker enzyme of liver parenchyma damage, was assessed twenty-four hours later. Reducing of enzyme amount by more than 30% relative to the control group was considered as evidence of hepatoprotective properties of the substance.

Silymarin in a dose of 100 mg/kg was used as a reference agent. Experimental results are shown in Table 18.

TABLE 18

Assessment of hepatoprotective activity of the claimed substances.

| Substance | AlAT, mmol/l/h | % of reducing AlAT |
|---|---|---|
| Intact | 0.27 ± 0.04 | — |
| $CCl_4$ | 0.83 ± 0.21 | — |
| VIII | 0.48 ± 0.19 | −42 |
| XXVII | 0.42 ± 0.08 | −49 |

TABLE 18-continued

Assessment of hepatoprotective activity of the claimed substances.

| Substance | AlAT, mmol/l/h | % of reducing AlAT |
|---|---|---|
| XXIX | 0.40 ± 0.04 | −52 |
| Silymarin | 0.38 ± 0.05 | −54 |

Experiment 14. Determination of Antioxidant Action of the Claimed Compounds

To assess a general antioxidant activity the method of riboflavine chemiluminescence was used. The test substance was introduced into a system consisted of phosphate buffer (pH 9.1), solution of riboflavine, and solution of bivalent iron sulfate. Chemiluminescence was initiated by 0.1% solution of hydrogen peroxide and registered by means of luminometer. A substance concentrations suppressing hemiluminescence by 50% were determined. Ascorbic acid was used as a reference agent. Experimental results are shown in Table 19.

TABLE 19

Assessment of antioxidant action of tbe claimed substances.

| Substance | Solvent | $IC_{50}$, µg/ml |
|---|---|---|
| XXVII | water | 13.00 |
| XXXII | water | 6.40 |
| XLII | water | 9.99 |
| Ascorbic acid | water | 2.39 |

Industrial Applicability

Examples 1–3 and results of practical synthesis and analysis of the claimed substances given in tables 1–5 confirm possibility of laboratory and industrial synthesis of all the forty nine claimed substances by the means that have been leant by modem pharmaceutical industry, and also their clear identification by commonly used control methods.

Series of experiments on determination of biological activity presented above in fourteen reports about combined experiments (Tables 6–19) have shown, that the claimed compounds possess biological activity in respect to various microorganisms including mycobacteria, chlamydia, Herpes Simplex virus, and they also possess interferon-inducing activity, antiaggregational, antiatherosclerotic, psychostimulative, psychodepressive, analgesic, hypoglycemic, antiulcerous, hepatoprotective, and antioxidant activities. The latter indicates the possibility of their use for treatment of various viral diseases and some oncological diseases. Besides that, a series of experiments has demonstrated that the claimed substances possess some other kinds of biological activities the possibility to use them in the cases of diabetes, pain syndrome, myocardial infarction and other diseases.

The presented facts prove that the objectives stated by the invention is achieved: a group of new chemical compounds, which are derivatives of 5-oximinobarbituric acid, was synthesized, and these derivatives possess high and expand biological activity, and particularly antibacterial (against tuberculosis and mycobacteriosis), immunostimulating, antichlamydial, antiviral, antituberculous, antiaggregational, psychostimulative, psychodepressive, antioxidant, analgesic, hypoglycemic, antiatherosclerotic, antiulcerous, and hepatoprotective activities Therefore, according to our opinion, the claimed substances satisfy all the demands that are imposed upon an invention: they are new, not obvious, and industrially applicable.

LITERATURE

[1]. Pharmaceutical microbiology, Ed. by W. B. Hugo and A. D. Russel. Blackwell Scientific Publications, Oxford, 1987, 511p.
[2]. Saltzmann R., Jurewicz R., Boon B, Safety of Famciclovir in patients with herpes zoster and genital gerpes, Antimicrobial Agents and Chemotheraphy, 1994, Vol.38, No. 10, P. 2454–2457.
[3]. Mashkovsky, M. D., "Drug means" (in Russian). Part 2, Moscow: "Medicina", 1993, 688 p.
[4]. PCT application PCT/RU95/00079 (WO 96/07423, Mar. 14, 1996) O. Travkin and D. Genkin. Immune-modulating remedy.
[5]. Negwer M., Organic-chemical drugs and their synonims, Academic-Verlag. Berlin, 1987.
[6]. Bojarski J. T., Mockrosz J. L., Barton H. J., Paluchowska M. H. Advances in Het. Chem., Ed. by A. R. Katritzky, 1985, V.38, P. 229–297.
[7]. Spasov A. V., Raikov Z. D., Author's Certificate of Bulgaria No. 17122, Int. cl. C 07 D 51/22, appl. Jun. 5, 1971.
[8]. Ueda T., Kato S., Japan patent 11832, Aug. 23, 1962, appl. 10.05.1958.
[9]. Misra V. S., Khan M. A., Srivastava N., Verma H. N., Current Science, V.55, No. 23, P.1167–1171.
[10]. Krepelka J., Kotva R., Pijman V., Semonsky M., Czechoslovakia patents NN 215554; 215593; 215580, Int. cl. CO7D 239/54; Apr. 15, 1984.
[11]. Ukita C., Japan patent 1445, Feb. 14, 1964, appl. Feb. 11, 1960.
[12]. Biswas C. Dissert. Abstracts 1964, Vol.24, No. 9, P.3501.
[13]. Langley B. W., Britain patent No. 845378, Aug. 24, 1960.
[14]. Eiden F., Kucklaender U. Ger. Offen 1.944.419 Int. cl. C07 D, A61k, Mar 11, 1991, appl. Sep. 2, 1969.
[15]. Blythin D. J., Coldwell N. J., U.S. Pat. No 4,272,535, publ. 09.07.1981 (appl. 27.07.79).
[16]. Hantzsch A., Isherwood P. C., Chem. Berichte, 1909, B.42, S. 986–1000.
[17]. Ziegler M., Glemser O., Microchim. Acta, 1956, No 10, S.1515–1517.
[18]. Ligten J. W., Velthuyzen H., Microchim. Acta, 1964, No 5, S.759–763.
[19]. Burbello A. T. Author's abstract of thesis. Moscow 1992, 40 p.
[20]. Burbello F. T. et. al. Author's certificate of USSR No. 4774701. appl. Jan. 15. 1989.
[21]. Shugaley E. V. et.al. Journal of Gen. Chem. (in Russian), 1993. v.63, iss.7, p.1646–1650.
[22]. Fischer E., Diltey A., Lieb. Annalen, 1904, B.335, S. 334–368.
[23]. Senda S., Fujimura H., Izumi M., Japan patent 29.856, Dec. 22, 1964, appl. Oct. 5, 1961 (4 pp).
[24]. Vishnjakova T. E. et.al. Uspekhe himii (Sucsesses of Chemistry, in Russian) 1985. T.LIV, p.429–449.
[25]. Irwin S., Psychopharmacology, 1968, 13,222–257
[26]. Gentry G. A., Lawrency N., Lushbaugh N. Isolation and differentiation of Herpes Simplex virus and Trichomonas vaginalis in cell culture, J. of Clinical Microbiology 1985, Vol. 22, No. 2, P. 199–204
[27]. Wang S-P., Grayston J. T. Serotyping of Clamydia trachomatis by inderect fluorescent-antibody staining of inclusions in cell culture with monoclonal antibodies. J. of Clinical Microbiology, 1991, Vol.29, No. 7, P.1295–1298.
[28]. Judson B. A., Lambert P. P. Improved Syva MicroTrac Clamydia trachomatis direct test method, Journal of Clinical Microbiology, 1988, Vol.26, No. 12, P.2657–2658.

What is claimed is:

1. A compound having the formula

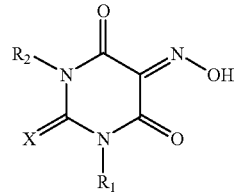

where

X is sulfur;

$R_1$ is selected from the group consisting of saturated or unsaturated alkyl, cycloalkyl, aryl and arylalkyl; and, $R_2$ is selected from the group consisting of hydrogen, saturated or unsaturated alkyl, cycloalkyl, aryl and arylalkyl.

2. The compound of claim 1 wherein $R_1$ is Et, and $R_2$ is H.

3. The compound of claim 1 wherein $R_1$ is n-$C_6H_{13}$, and $R_2$ is H.

4. The compound of claim 1 wherein $R_1$ is cyclohexyl, and $R_2$ is H.

5. The compound of claim 1 wherein $R_1$ is allyl, and $R_2$ is H.

6. The compound of claim 1 wherein $R_1$ is $CH_3$, and $R_2$ is $CH_3$.

7. The compound of claim 1 wherein $R_1$ is Et, and $R_2$ is Et.

8. The compound of claim 1 wherein $R_1$ is o-$CH_3C_6H_4$, and $R_2$ is H.

9. The compound of claim 1 wherein $R_1$ is p-$CH_3C_6H_4$, and $R_2$ is H.

10. The compound of claim 1 wherein $R_1$ is o-$FC_6H_4$, and $R_2$ is H.

11. The compound of claim 1 wherein $R_1$ is p-$FC_6H_4$, and $R_2$ is H.

12. The compound of claim 1 wherein $R_1$ is p-$ClC_6H_4$, and $R_2$ is H.

13. The compound of claim 1 wherein $R_1$ is p-$(CH_3O)C_6H_4$, and $R_2$ is H.

14. The compound of claim 1 wherein $R_1$ is p-$(CH_3O)C_6H_4$, and $R_2$ is Ph.

15. The compound of claim 1 wherein $R_1$ is o-$(CH_3)C_6H_4$, and $R_2$ is o-$(CH_3)C_6H_4$.

16. The compound of claim 1 wherein $R_1$ is p-$(CH_3O)C_6H_4$, and $R_2$ is p-$(CH_3O)C_6H_4$.

* * * * *